(12) United States Patent
 Simonson et al.

(10) Patent No.: US 10,751,192 B1
(45) Date of Patent: *Aug. 25, 2020

(54) METHOD OF INSERTING A SURGICAL IMPLANT WITHIN A TRANSCORPOREAL VOID

(71) Applicants: Robert E. Simonson, Boca Raton, FL (US); David P. Sachs, Boca Raton, FL (US)

(72) Inventors: Robert E. Simonson, Boca Raton, FL (US); David P. Sachs, Boca Raton, FL (US)

(*) Notice: Subject to any disclaimer, the term of this patent is extended or adjusted under 35 U.S.C. 154(b) by 94 days.

This patent is subject to a terminal disclaimer.

(21) Appl. No.: 16/037,671

(22) Filed: Jul. 17, 2018

Related U.S. Application Data

(63) Continuation of application No. 15/643,368, filed on Jul. 6, 2017, now Pat. No. 10,064,735.

(51) Int. Cl.
  *A61F 2/44* (2006.01)
  *A61F 2/30* (2006.01)
  *A61F 2/46* (2006.01)

(52) U.S. Cl.
  CPC .............. *A61F 2/44* (2013.01); *A61F 2/4611* (2013.01); *A61F 2002/30261* (2013.01); *A61F 2002/30593* (2013.01)

(58) Field of Classification Search
  CPC .................................... A61F 2/44; A61F 2/447
  See application file for complete search history.

(56) References Cited

U.S. PATENT DOCUMENTS

| 5,591,235 A | * | 1/1997 | Kuslich | ................. | A61B 17/70 |
| | | | | | 606/261 |
| 8,879,934 B2 | * | 11/2014 | Kameda | ............ | G03G 15/2028 |
| | | | | | 399/322 |

* cited by examiner

*Primary Examiner* — Andrew Yang
(74) *Attorney, Agent, or Firm* — Burr & Forman LLP; Jeffrey H. Kamenetsky

(57) ABSTRACT

An implant preshaped before placement anteriorly between a superior endplate and an inferior endplate within a void created by a transcorporeal procedure in a vertebra, the implant having no circular cross-sectional dimension.

3 Claims, 8 Drawing Sheets

METHOD OF INSERTING A SURGICAL IMPLANT WITHIN A TRANSCORPOREAL VOID

CROSS-REFERENCE TO RELATED APPLICATION

This application claims the benefit of U.S. patent application Ser. No. 15/643,368, filed on Jul. 6, 2017, which is incorporated herein by reference in its entirety.

STATEMENT REGARDING FEDERALLY SPONSORED RESEARCH OR DEVELOPMENT n/a

TECHNICAL FIELD

The present disclosure relates to surgical implants and in particular to an implant used for repairing a defect created in the performance of a surgical procedure.

BACKGROUND

In the field of anterior spinal surgery, a current procedure being performed is called a transcorporeal procedure. This procedure has been recognized as a viable option for addressing pathologies that rest behind the anterior portion of a vertebra known as the vertebral body, also referred to as the "vertebral corpus." The pathologies addressed by the transcorporeal procedure are generally around or anterior to the spinal cord or other neural anatomy. The creation of a small hole in the bone of the vertebral body is intended to give the surgeon access to pathology and anatomy in the anterior to central portions of the spine. One of the goals of this procedure is to allow a surgeon to reach across bone to locate and treat pathology affecting a patient without performing a fusion of two vertebral bodies.

This general anatomical area where pathologies exist that are addressable by the transcorporeal procedure include the posterior portions of the vertebral body, the posterior portions of the vertebral endplates, the ligament called the posterior longitudinal ligament, the spinal cord and the spinal canal. This general area will be referred to herein as the "greater anterior epidural space" and/or the "greater epidural space." This area would necessarily include the nerve roots that traverse the spine, the neural foramen of vertebra, the posterior portions of the intervertebral discs and any pathology that occurs in this area as well as the area itself. Thus, for clarity, "the greater epidural space" can be defined as including posteriorly, the area of anatomy beginning with and including the spinal cord and canal with the canal's contents, to the posterior half of a vertebral body.

One of the procedures attempting to address pathologies in the greater epidural space is called a transcorporeal approach. In a transcorporeal approach, the vertebral body is left in place and a small hole is drilled into and through the corpus of the vertebra. Many surgeons refer to the hole as a surgically created vertebral defect. Therefore the word "defect" may be used interchangeably with "hole" or "void" herein. A feature of the transcorporeal approach is the drilling of a small round hole into the vertebral body beginning anteriorly and directed posteriorly creating an exit at the back of the vertebral body. The trajectory of this hole is such that if performed properly the posterior terminus of the hole is adjacent to the pathology being targeted by this procedure. In a transcorporeal approach, it is through this hole that the surgeon performs a procedure that treats a pathology residing behind the vertebra. Therefore, a transcorporeal hole is actually not just a hole but a functional pathway in which a surgeon performs a procedure.

The transcorporeal approach differs from older, more common standards of care and approaches in spinal surgery in that it is not an inter-vertebral procedure. When used as a prefix, "inter" means "between." Transcorporeal means the procedure does not go between two vertebral bodies; it goes through a single vertebral body. "Intervertebral" is when a surgical procedure goes between two vertebral bodies. In other words, the procedure goes through a space created by removing an intervertebral disc from between two vertebrae. In an intervertebral approach, an intervertebral implant is normally placed against the remaining external aspects of two vertebrae, between the two vertebrae, against what may remain of the external aspect of an inferior endplate of one vertebra and what may remain of the external aspect of a superior endplate of another vertebra. This type of intervertebral approach usually requires an implant to replace the disc.

The goal of a transcorporeal approach is to avoid disrupting the disc as much as possible and does not include fusing two vertebrae together. Therefore, the goals and function of an implant for transcorporeal repair is different than the goals and function of an implant for intervertebral fusion or disc replacement. A surgeon performs a transcorporeal procedure in order to preserve the disc.

A problem with a typical transcorporeal approach has been the extremely limited exposure to the anatomy and pathologies this approach provides the surgeon. As the name implies, and current technique teaches, in order to be transcorporeal, the body must be left in place or at least mostly in place in order to work through it and then go on to heal after the surgery is complete. The surgeon must necessarily limit his exposure to working through a tiny drill hole. This limitation to the transcorporeal approach has limited the procedure's adoption and success rate, making it entirely impractical on a large clinical scale. Hence, the transcorporeal approaches are only available to a limited number of patients with very limited pathologies.

Another problem with a typical transcorporeal approach is that if the hole drilled into a vertebral corpus is large enough to provide the significant access most pathologies require, the corpus will not be able to naturally fill the defect back with bone, as it will if the drill hole is kept small. A hole too large for bone to naturally grow back into, ends up leaving the patient with the potential of a vertebral body collapse, fracture, or any of a series of negative long term outcomes. If the hole created is small enough to grow back naturally as part of the body's normal healing pattern, the surgeon is not provided enough space to perform most of the surgical procedures necessary to treat the most common pathologies.

Thus, there is a need for providing an implant that may be used for repairing a substantial defect created in the performance of a transcorporeal surgical procedure. In order to fill the need, the implant must be capable of allowing for the repair of significantly larger and/or more variable defects that may be created in the course of performing a transcorporeal procedure.

SUMMARY

The implant of the present disclosure is for placement into a transcorporeal defect in order to repair a defect created within the confines of one vertebra, and not between two vertebrae, and to avoid the need to fuse two vertebrae together.

The implant of the present disclosure is placed between the internal aspects of the endplates of one vertebra; more accurately described as placed within a single vertebra, into the body or created defect in a vertebra, below the superior endplate and above the inferior endplate of one vertebra. This is different than intervertebral surgeries, discussed above. Phrased differently, the implant of the present disclosure is placed into the vertebral body of one vertebra to fill a transcorporeal defect or hole. By contrast, an intervertebral implant is placed between two vertebrae replacing a removed intervertebral disc.

The implant of this disclosure incorporates a number of inventive features that changes the nature of the limitations of what is referred to as a transcorporeal approach while treating pathology located behind the vertebral body and/or the disc space by working through the vertebra during a surgery utilizing an anterior approach without fusing two vertebrae together. The inventive features of the implant disclosed herein will allow for improvements in surgical techniques that will go beyond what has been known or thought about the traditional transcorporeal approach.

By eliminating some of the features of today's transcorporeal techniques and by providing a new implant with new inventive features, the present disclosure expands the current state of transcorporeal approaches which utilize a small round trajectory based hole in the vertebra, to a broader repairable technique for treating pathology beyond the posterior cortical wall of the vertebral body and into the greater epidural area. The features of the implant of the present disclosure and method of inserting the implant disclosed herein will give surgeons more freedom in the creation of the vertebral transcorporeal defect instead of the more traditional transcorporeal drill hole while still keeping within the original goals of the transcorporeal approach.

The implant of the present disclosure is configured to repair the hole or pathway in a vertebra created by a transcorporeal approach without the requirement that large portions of the vertebral corpus remain intact. Further, the implant of the present disclosure does not require a point of fixation for a trajectory guidance apparatus external to the defect.

As discussed herein, the features of the inventive implant of the present disclosure will give surgeons more choices and more freedom when creating, using, and then repairing a vertebral defect used during a transcorporeal procedure. Features of the implant described herein also allow for alternate techniques for inserting the implant and engaging the transcorporeal defect for repair. The inventive implant of this disclosure will give the surgeon flexibility to address a wider range of pathology than what is allowed by current transcorporeal approaches.

In one aspect of the disclosure, an implant is provided where the implant is preshaped before placement anteriorly between a superior endplate and an inferior endplate within a void created by a transcorporeal procedure in a vertebra, the implant having no circular cross-sectional dimension.

In another aspect of the disclosure, an implant is provided where the implant is preshaped before placement anteriorly between a superior endplate and an inferior endplate within a void created by a transcorporeal procedure in a vertebra, the implant having a circular cross-sectional dimension.

In another aspect of the disclosure, an implant for placement anteriorly between a superior endplate and an inferior endplate within a transcorporeal void in a vertebra is provided, where the implant has no circular cross-sectional dimension. The implant includes an engagement mechanism for engaging the implant with an innermost surface of the vertebra, an open region configured to receive a patient's blood, the implant further secured within the void due to coagulation of the patient's blood, a first dimension having a first dimensional length, a second dimension having a second dimensional length, and a third dimension having a third dimensional length, wherein at least two of the first dimensional length, the second dimensional length, and the third dimensional length are at least fifty percent of a shortest cross sectional measurement of the vertebra, and a cross sectional dimension that is greater than a cross sectional dimension of the void, wherein after insertion into the void in the vertebra, greater than fifty percent of a mass of the implant resides within the vertebra. Further, the open region allows for the placement or packing of the patient's own bone or a suitable substitute to further secure or fixate the implant within the void.

In another aspect of the disclosure, a method of placing an implant into an iatrogenically created spinal defect, the defect created during a transcorporeal procedure to the spine, is provided. The method includes placing the implant between a superior endplate and an inferior endplate of a single vertebra such that the superior endplate and the inferior endplate remain functionally intact, the implant placed such that greater than fifty percent of the implant resides within the spinal defect.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
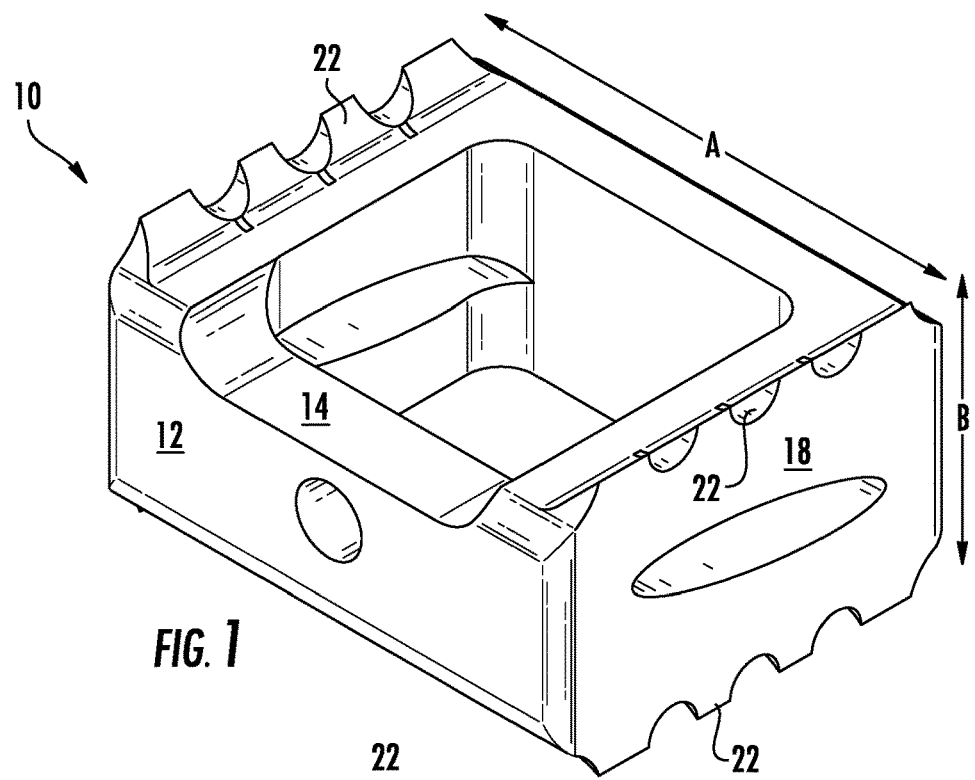
FIG. 1 illustrates a perspective view of the surgical implant of the present disclosure.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

In one embodiment, an inventive implant is provided that does not require a presence outside of the confines of the vertebra itself. In one embodiment of the implant of the present disclosure, there are no tabs or features outside the confines of the vertebral body or defect therein. In another embodiment, there are small tabs or features that rest against the remaining bone of the anterior aspect of the vertebra, but the mass of the implant resides mostly if not completely within the confines of the vertebra itself and or the defect itself.

In one embodiment, after placement into the vertebral defect, greater than fifty percent of the mass of the implant resides within the confines of the vertebral body. In another embodiment, greater than fifty percent of the implant resides within the confines of the vertebral defect. In other embodiments, the width of the implant is greater than thirty percent of the width of the vertebral body having a transcorporeal defect.

The implant disclosed herein does not require a large presence outside of the confines of the vertebral body itself. There are several features of the disclosed implant that allows for this aspect of the implant. With the ability to insert the entire implant or the majority of the implant within the confines of the vertebral body and/or the vertebral defect, the disclosed implant allows for the removal of more bone, thereby creating a larger and more variable transcorporeal defect. Any bone required for implant fixation is bone that cannot be removed for accessing anatomy or pathology. With the greater percentage of this implant resting within the confines of the vertebra, the surgeon does not need to worry that too much bone is being removed during the course of treating the patient. The feature of the greater portion of the disclosed implant residing within the confines of the vertebra means that a larger portion of the vertebral body may be removed as part of the exposure for treating whatever pathologies are troubling the patient. Thus, there is no need to attach a bone plate to the outside of the vertebra through which the implant is to be inserted or to provide a screw outside of the original intended defect used in the performance of the actual transcorporeal procedure treating the pathology. This freedom of surgical dissection allows a surgeon to remove a portion of the vertebral body up to and including the entirety of the vertebral body as the surgeon sees fit for the patient's benefit. Removing up to the entirety of the vertebral body means at a surgeon's discretion, the surgeon could remove up to everything between the interior edges of two endplates of a single vertebra.

Disclosed herein is an implant where after its placement into the transcorporeal defect, greater than fifty percent of the implant resides within the confines of the vertebral body. In certain embodiments, greater than thirty percent of the implant resides within the confines of the vertebral body. The term "within the confines of the vertebral body" shall mean, herein, within the cortical walls of the vertebra not resting outside of the cortical walls of the vertebra. In some embodiments, further discussed below, portions of the implant such as, for example, blades, engage the vertebral bone and do so while maintaining a presence within the confines of the cortical wall of the vertebra. When the blades of the implant engage the bone of the vertebra within the confines of the vertebra, the bone engaged is bone that remains outside the edge of the defect. In other words, it is bone that is left after the creation of the transcorporeal defect. Embodiments of this implant as described will have a larger presence within the defect itself and have less blade attachment to bone outside of the defect. Here we disclose an implant wherein greater than fifty percent of the implant resides within the confines of the defect created in the performance of a transcorporeal approach. This is significant because any engagement outside of the defect itself requires bone left in place during the creation of the transcorporeal defect. Every bit of bone left in place during the creation of the defect makes the hole, and therefore the exposure smaller giving the surgeon less room to operate. In both embodiments described in this section greater than fifty percent of the implant is within the confines of the cortical walls of the vertebra upon which the transcorporeal procedure is being performed.

Referring now to FIG. 1, an exemplary embodiment of the surgical implant 10 of the present disclosure is illustrated. Implant 10 includes a front portion 12, a top portion 14, a first side portion 16 (not shown), a second side portion 18, a rear portion 20 (not shown), and a bottom portion 21 (not shown). In one embodiment, implant 10 is preshaped before placement anteriorly between a superior endplate and an inferior endplate within a void created by a transcorporeal procedure in a vertebra, the implant 10 having no circular cross-sectional dimension.

In another embodiment, implant 10 includes an engagement mechanism for engaging the implant 10 with at least one inner surface of the vertebra. The engagement mechanism could be, for example, a series of blades 22 that extend from an exterior of the implant 10, the blades 22 configured to engage with at least one inner surface of the vertebra. Blades 22, which are discussed in greater detail below, can be disposed along the lower and/or upper edges of at least one of the first side portion 16 and second side portion 18. Although the embodiment shown in FIG. 1 includes four sets of blades 22 (the blades along the lower edge of first side portion 16 are not shown), it is within the scope of the present disclosure to provide an implant having less or more than the number of blades shown in FIG. 1. In other embodiments, implant 10 does not include any blades. Implant 10 may be made of any metal, biological, biologically compatible, synthetic or natural materials, including bone or bone and tissue substitutes.

In this embodiment, a first dimensional length "A" between first side portion 16 and second portion 18 is considered to be the "width" of implant 10, while a second dimensional length "B" represents the height of implant 10. In the embodiment depicted in FIG. 1, the width A of implant 10 is greater than the height B of implant 10. In one embodiment, implant 10 is selected from a plurality of available implants 10 where the plurality of available implants 10 includes implants 10 of varying heights, widths, and lengths, and also varying ratios of height to width to length. In other embodiments, the first dimensional length "A" is less than the second dimensional length "B" while in some embodiments the first dimensional length "A" of implant 10 equals the second dimensional length "B" of implant 10.

Providing an implant 10 or a series of implants 10 where the width is equal to or greater than the height of the implant 10, allows a surgeon performing an anteriorly based surgical procedure upon the spine of a patient the freedom to follow an operative plan that allows the surgeon to remove considerably more bone than what would be permitted by a transcorporeal approach today. Additionally, the feature of width being equal to or greater than the height of implant 10 eliminates the requirement of the surgeon to use a round drill bit or trephine or any other tool that will limit the surgeon to the creation of a vertebral defect that is round or mostly round in shape. This design feature will provide surgeons the ability to significantly expand the selection of tools for bone removal and permit the creation of a spinal defect wherein the shape of the defect is dictated only by anatomy, pathology, or surgeon preference, not round to fit a tool, or an implant, or necessarily small to leave enough space on the vertebra to allow for a large plate to be attached to the front of the vertebral body.

In another embodiment, if the patient's anatomy and/or pathology, and/or the surgeon preference dictate, the ratio of width to height of implant 10 could be reversed for the patient's benefit. Therefore, in another embodiment, implant 10 or a series of implants 10 are provided where the height B of implant 10 is equal to or greater than the width A of implant 10. Recognizing that the vertebral body is a large block of bone and that the patient's anatomy and pathology may vary from the norm, it is possible that a surgeon may find the need to work in a different direction. In other words, if variation in the patient's anatomy or pathology prompts a surgeon to work more superior to inferior or vertical in trajectory, the surgeon may decide implant 10 needs to be placed on its side or in some other orientation than the orientation shown in FIG. 1. For example, many or most of the common pathologies reside behind the disc, on the edges of the vertebral endplates, and often in or around the neural foramen. These pathologies are usually fixed in location and during surgery the surgeon will find them where they appeared on the image studies. These pathologies would often lead a surgeon to create a transcorporeal defect wherein the largest dimension is across the vertebral body from side to side.

A number of patients requiring surgery may have a pathology requiring a modification in the creation of the transcorporeal defect. In these cases, the surgeon may create the transcorporeal defect along an altered axis. In order to try to benefit all patients, or more patients, the surgeon needs to be prepared for these types of cases when they appear. A single example of this, of which there could be many, is what is referred to a free fragment. A free fragment describes a piece of intervertebral disc that is no longer attached to the disc. The fragment is freely floating or moving around within the greater epidural space. This fragment can be found in a location behind posterior to the vertebra. Once located, this free disc fragment can be grasped and removed. In these cases, the surgeon is not assured that the fragment is exactly where it was during the initial image study. The fragment may have moved. By utilizing the inventive implant 10, the surgeon is provided with the ability to address variables that may occur during this type of case. In this type of example, the surgeon could rotate, angle, or flip implant 10 on its side and place it into the void. For these reasons, the ratios may be maintained as described in other embodiments, but may also be reversed from width to height over to height to width. In this embodiment, implant 10 will have a height that is equal to or greater than its width.

Figure 2:
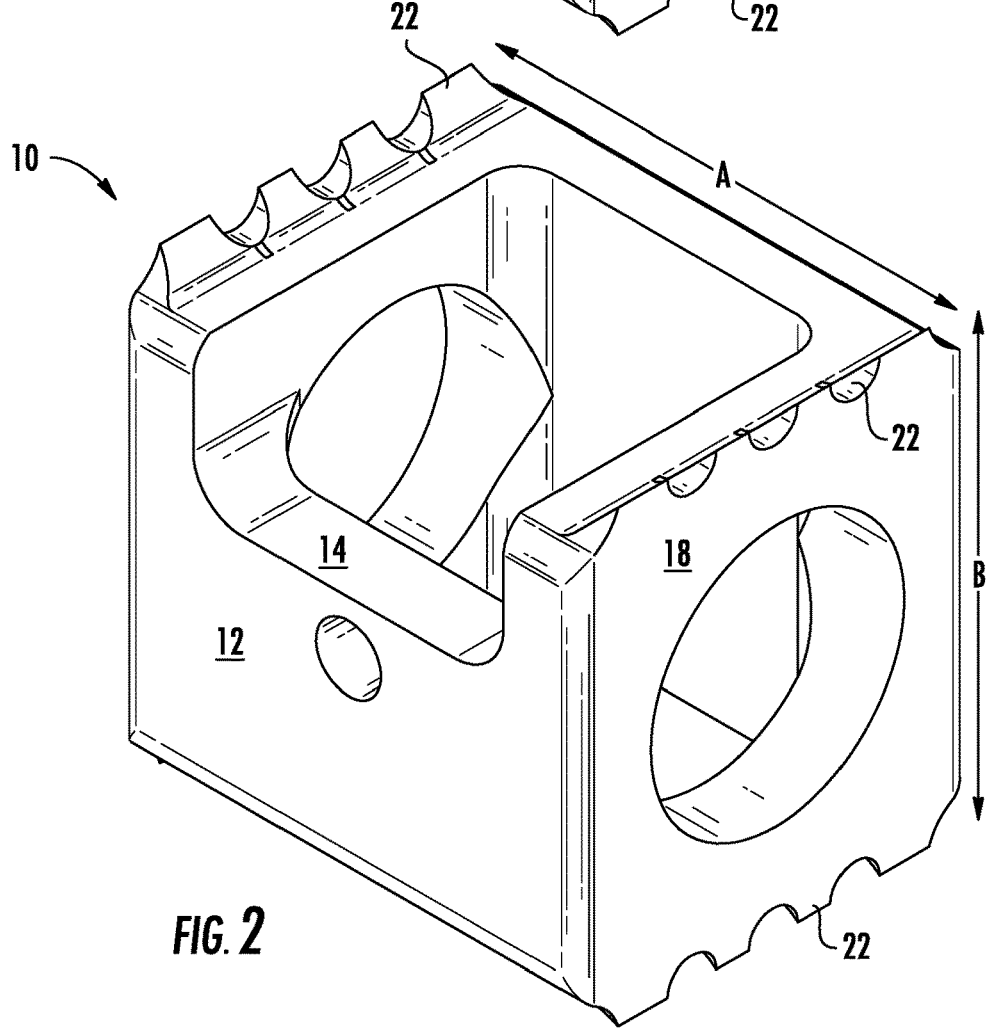
FIG. 2 illustrates a perspective view of an alternate embodiment of the surgical implant of the present disclosure.

FIG. 2 is an illustration of another embodiment of implant 10, where width A of implant 10 is substantially equal to height B of implant 10. Implant 10 of the present disclosure may include widths A and heights B of any range. Thus, there is no limitation of any specific width or height of implant 10, nor is there any limitation of the ratio between the width of implant 10 and the height of implant 10. For example, implant 10 may have the following dimensions: 12 mm width×6 mm height; 12 mm width×7 mm height; 12 mm width×8 mm height; 12 mm width×9 mm height; 12 mm width×10 mm height; 12 mm width×11 mm height; 12 mm width×12 mm height (width is equal to height in this embodiment); 14 mm width×6 mm height; 14 mm width×7 mm height; 14 mm width×8 mm height; 14 mm width×9 mm height; 14 mm width×10 mm height; 14 mm width×11 mm height; and 14 mm width×12 mm height. The preceding dimensions of implant 10 are merely exemplary and show that the dimensions of implant 10 may vary.

Figure 3:
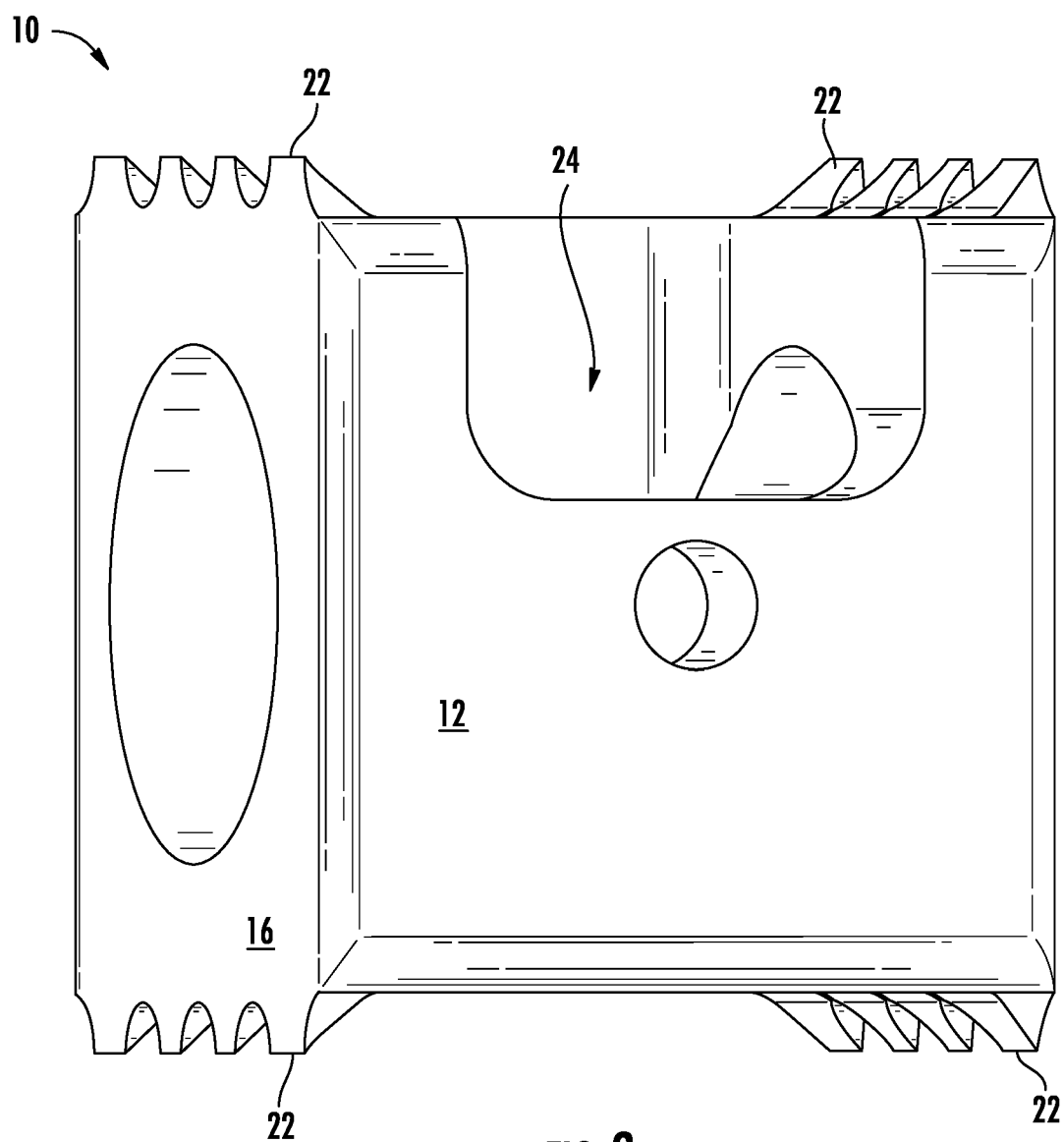
FIG. 3 illustrates a front perspective view of the alternate embodiment of the surgical implant of the present disclosure as shown in FIG. 2.

FIG. 3 shows a front perspective view of implant 10. Blades 22 are clearly seen protruding from the upper and lower edges of first side portion 16 and second side portion 18. Blades 22, as explained in further detail below, are used to engage the interior surfaces of the vertebral body. Implant 10 also includes open region 24. In one embodiment, open region 24 is filled at least partially with a biologically compatible graft material. For example, in one embodiment, the biologically compatible graft material is a cortical cancellous bone mixture from the patient. The creation of the transcorporeal defect through the bone of the vertebral body provides a significant amount of graft material. As bone is removed from the vertebra to create the defect, this bone is saved to be placed into open region 24 of implant 10 and put back in place within the vertebra. This removal of bone creates an environment wherein the remaining bone of the vertebra exudes a mixture of blood and bone related cells. When the biologically compatible graft material within open region 24 of implant 10 is introduced back into the bleeding bone of the remaining vertebra, the remaining bone begins to incorporate it. As the blood and cell mixture from the vertebra begins incorporating with the unimpeded open region 24 of implant 10 filled with the same blood and cell mixture removed only shortly before, the patient's body begins to secure the implant 10. This design feature provides a method of retaining implant 10 in place and obviating the need of an external plate or other method of external fixation.

In yet another embodiment, it may be beneficial to modify or remove the open region 24 and use a porosity within the implant 10 in conjunction with or in place of the open region 24. This porosity could be used to receive blood or blood cells and use the blood coagulation for fixation, holding implant 10 in place and using the growth factors included in the patient's blood to integrate implant 10 into the patient's vertebra 26.

Figure 4:
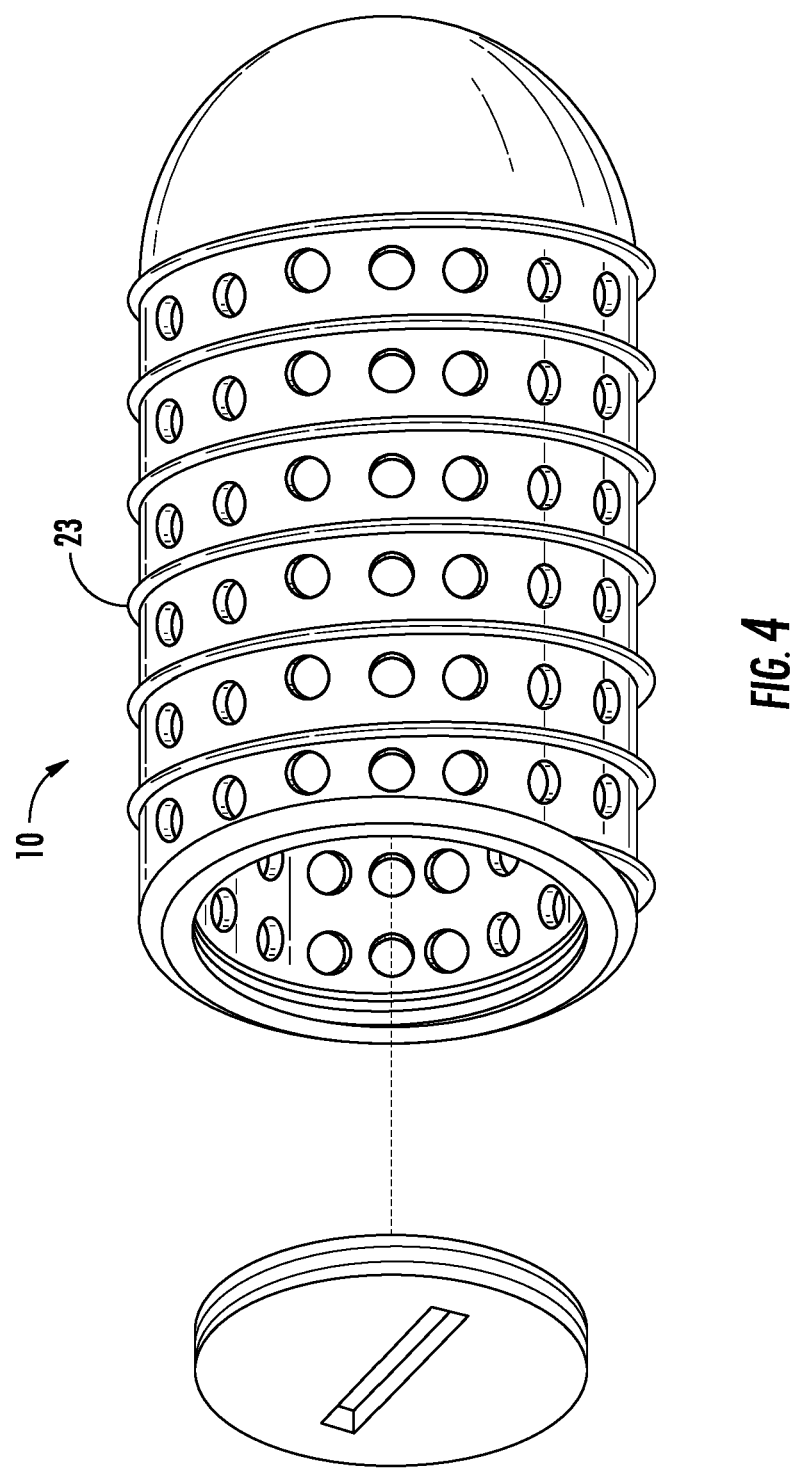
FIG. 4 illustrates a side view of an alternate cylindrical embodiment of the implant of the present disclosure.

FIG. 4 illustrates an alternate embodiment of the implant 10 of the present disclosure. In this embodiment, implant 10 is cylindrical in shape, i.e., this embodiment of implant 10 has a circular cross-sectional dimension. In one embodiment, the implant 10 shown in FIG. 4 is preshaped before placement anteriorly between a superior endplate and an inferior endplate within a void created by a transcorporeal procedure in a vertebra. In one embodiment, implant 10 includes an internal engagement mechanism for engaging the implant 10 with at least one inner surface of the vertebra, such as, for example, blades 22 or threads 23 (as shown in FIG. 4). As in the earlier embodiments, implant 10 may include an open region 24 configured to receive a patient's blood, the implant 10 further secured within the void due to coagulation of the patient's blood. In the cylindrical embodiment in FIG. 4, the open region 24 consists of a plurality of apertures.

In another embodiment, the implant 10 shown in FIG. 4 has an outer cross sectional dimension that is greater than a cross sectional dimension of the void into which the implant 10 is placed. In FIG. 4, cylindrical implant 10 has a first dimension, i.e., its length, having a first dimensional length and a second dimensional length, i.e., its diameter, having a second dimensional length, wherein the first dimensional length is greater than the second dimensional length. However, this embodiment is merely exemplary, and implant 10 may have a length having a first dimensional length, and a diameter having a second dimensional length, wherein the first dimensional length is equal to the second dimensional length. In other embodiments, the diameter is greater than the length of implant 10. In another embodiment, the implant 10 shown in FIG. 4, after its insertion into the void in the vertebra, has greater than fifty percent of its mass residing within the vertebra.

Figure 5:
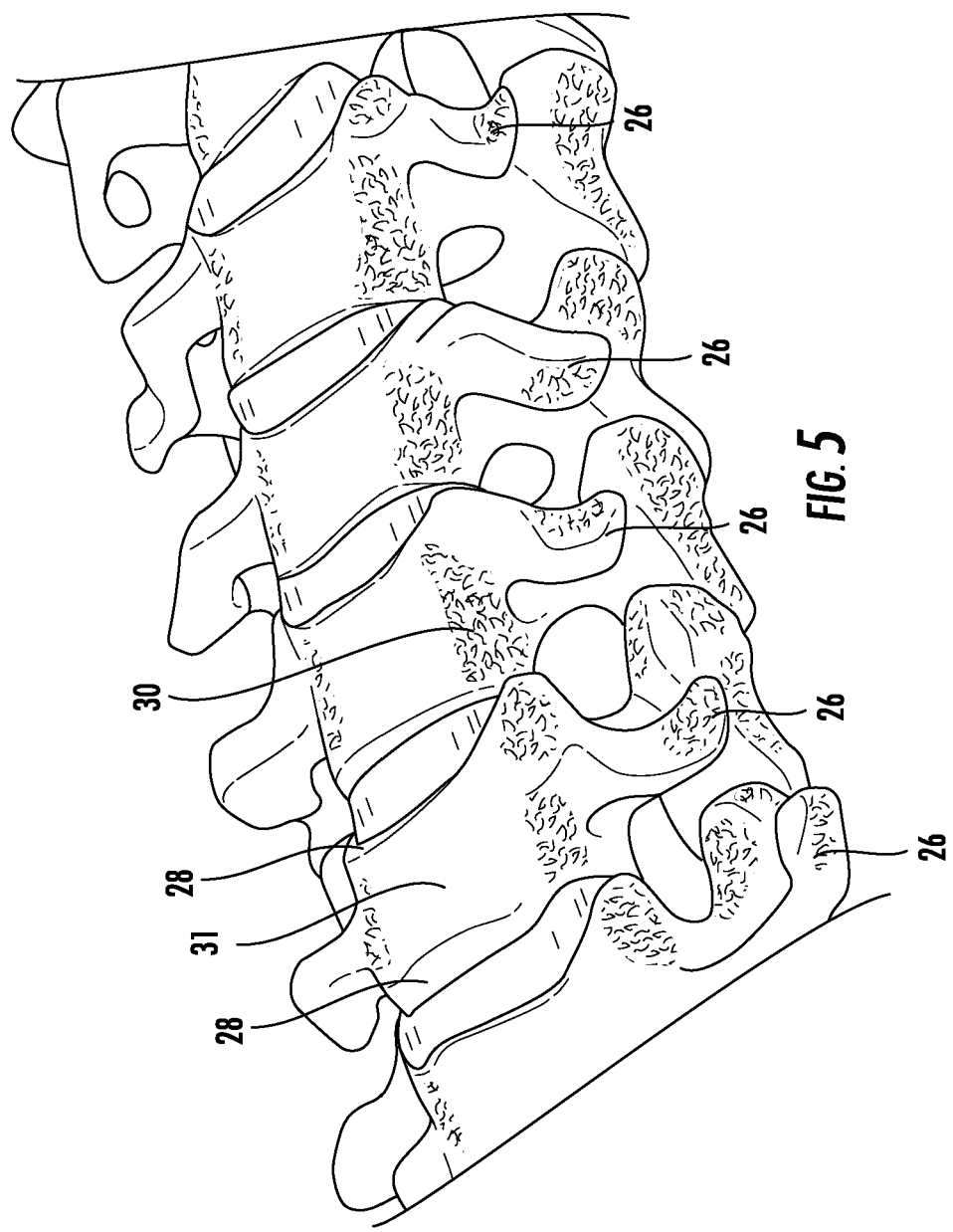
FIG. 5 illustrates a view of a series of adjacent vertebra.

FIG. 5 illustrates a series of adjacent vertebra 26 prior to a transcorporeal surgical procedure. Each vertebra 26 includes endplates 28 and lateral walls 30. Implant 10 is to be inserted into a void created within a single vertebra 26 by removal of the vertebral corpus portion 31 of the vertebra while leaving the endplates 28 and lateral walls 30 functionally intact.

Figure 6:
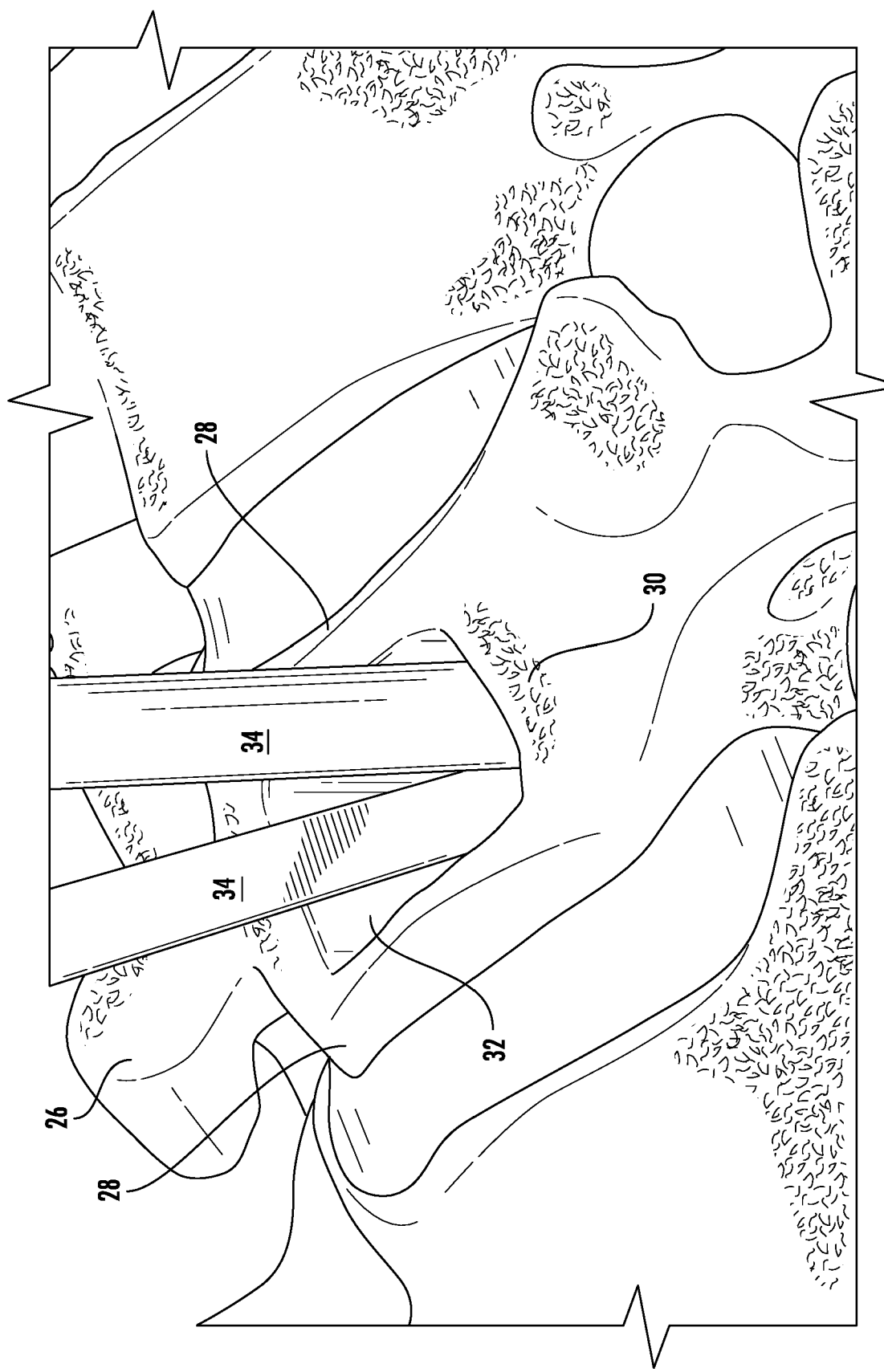
FIG. 6 illustrates a surgical procedure being performed within a void in a single vertebra.

FIG. 6 illustrates a single vertebra 26 in which the entirety of the corpus portion of the vertebra 26 has been removed, thus creating a void 32 into which implant 10 is to be inserted, and a surgical procedure being performed by at least one surgical instrument 34 within the created void 32. The endplates 28 and lateral walls 30 of vertebra 26 have not been significantly violated, nor has there been any significant violation of any of the adjacent vertebra 26. In another embodiment, a portion of the corpus portion 31 of the vertebra 26 is removed. Thus, it is within the scope of the present disclosure to insert implant 10 into a void created by a surgical instrument, where the entirety of the vertebral corpus 31 is removed or a portion of the vertebral corpus 31 is removed, where, in either event, the endplates and lateral walls of vertebra 26 are left functionally intact.

Figure 7:
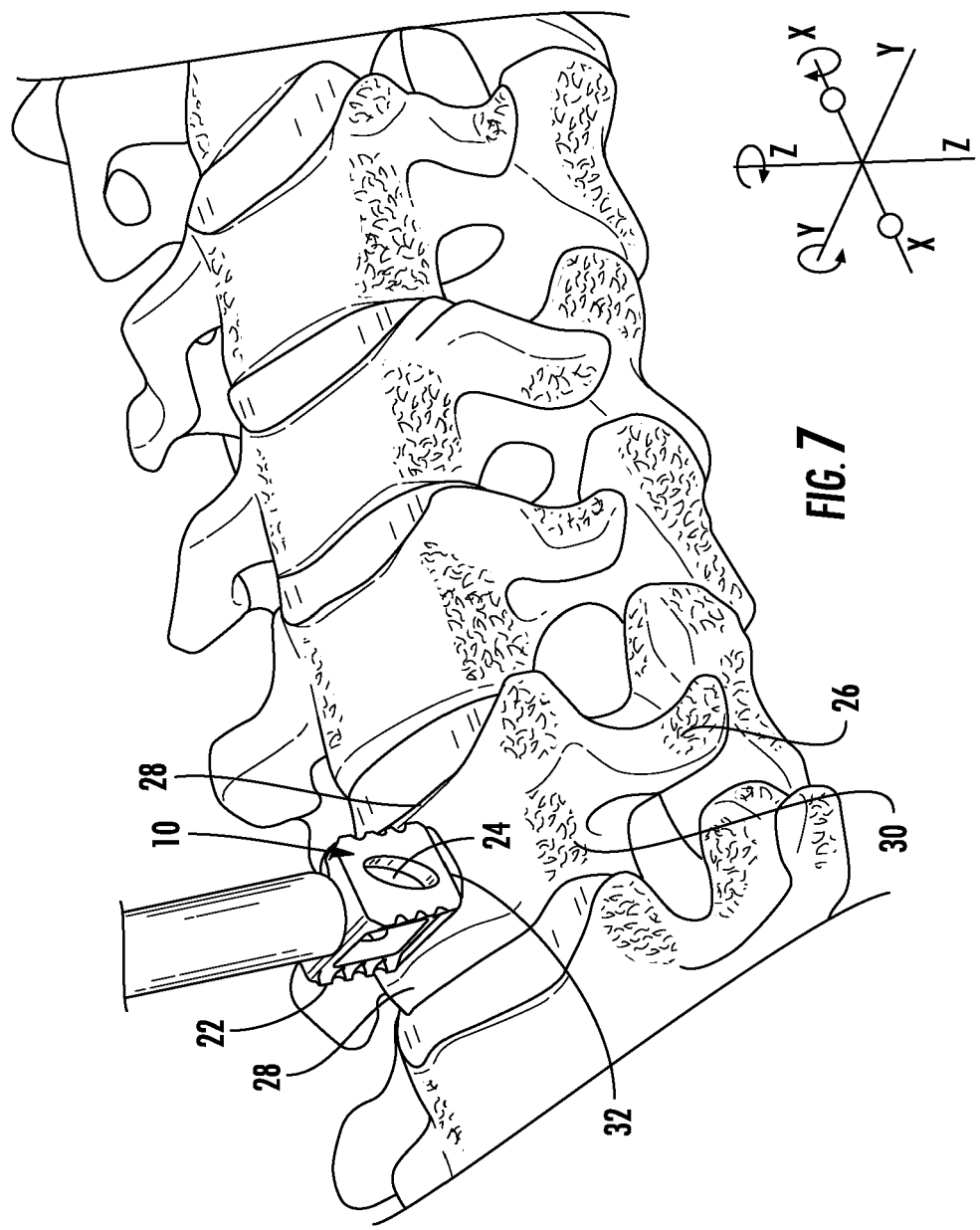
FIG. 7 illustrates the implant of the present disclosure about to be inserted within a void in a single vertebra.

FIG. 7 shows implant 10 in the initial stages of being inserted into void 32 within vertebra 26. Upon insertion within void 32, implant 10 engages one or more of the innermost surfaces of the void 32 or defect created by the surgical procedure. In one embodiment, implant 10 engages the innermost surface of the most superior aspect, inferior aspect, and/or lateral aspect of a vertebral defect created in the performance of an anterior transcorporeal surgical procedure to vertebra 26. In another embodiment, implant 10 engages the superior surface of the superior aspect of a transcorporeal vertebral defect created in the performance of an anterior surgical procedure to vertebra 26 and engagement to the inferior aspect of a vertebral defect created in the performance of an anterior transcorporeal surgical procedure to the same vertebra 26. In another embodiment, implant 10 engages the innermost surface of the most lateral aspects on either side of a vertebral defect created in the performance of an anterior surgical transcorporeal procedure to vertebra 26 and engagement to the innermost surface of the most inferior and superior aspect of a vertebral defect created in the performance of an anterior transcorporeal surgical procedure to vertebra 26. The term, "engagement" in the context of this disclosure, is defined as having a point of physical contact, i.e., implant 10 physically contacting the innermost surfaces of the remaining vertebral body that forms the exterior of void 32, and using the point of contact to provide resistance to movement of implant 10 after its insertion within void 32.

In one embodiment, implant 10 engages with at least one of the superior aspect, inferior aspect, and lateral aspects, via blades 22 which extend from implant 22. Blades 22 may extend from implant 10 at various angles and may be of various lengths. For example, in one embodiment, blades 22 are 0.75 mm in length. The present disclosure shall not be limited in any way to a particular size, angle, or dimension of blades 22. Although blades 22 may be situated along the upper and lower edges of first side portion 16 and second side portion 18 (as shown in FIGS. 1-3), this need not be the case. For example, in certain scenarios, implant 10 may not need a full set of blades 22 to secure engagement with the interior surfaces of vertebra 26. In another embodiment, instead of blades 22 being used as the engagement mechanism, the engagement mechanism of implant 10 includes one or more threads along an exterior of implant 10, threads configured to engage with at least one inner surface of vertebra 26. In another embodiment, implant 10 has an outside dimension that is larger than the defect in the vertebra 26 into which it will be placed. Thus, as shown in FIG. 7, implant 10 has dimensions that are larger than the dimensions of the void 32 into which the implant 10 is to be inserted. The larger dimension of implant 10 may be due to the inclusion of blades 22 or threads, or the dimensions of implant 10 may just be larger than the dimensions of the void 32 without regard to the blades or threads. Thus, in one embodiment, implant 10 is secured within void 32 via a "friction fit" due to the fact that the outer cross sectional dimension of implant 10 is greater than the cross sectional dimension of void 32. This serves to maintain and secure the orientation of implant 10 within void 32. In other embodiments, the implant 10 has a cross sectional dimension equal to or smaller than the cross sectional dimension of the void.

Figure 8:
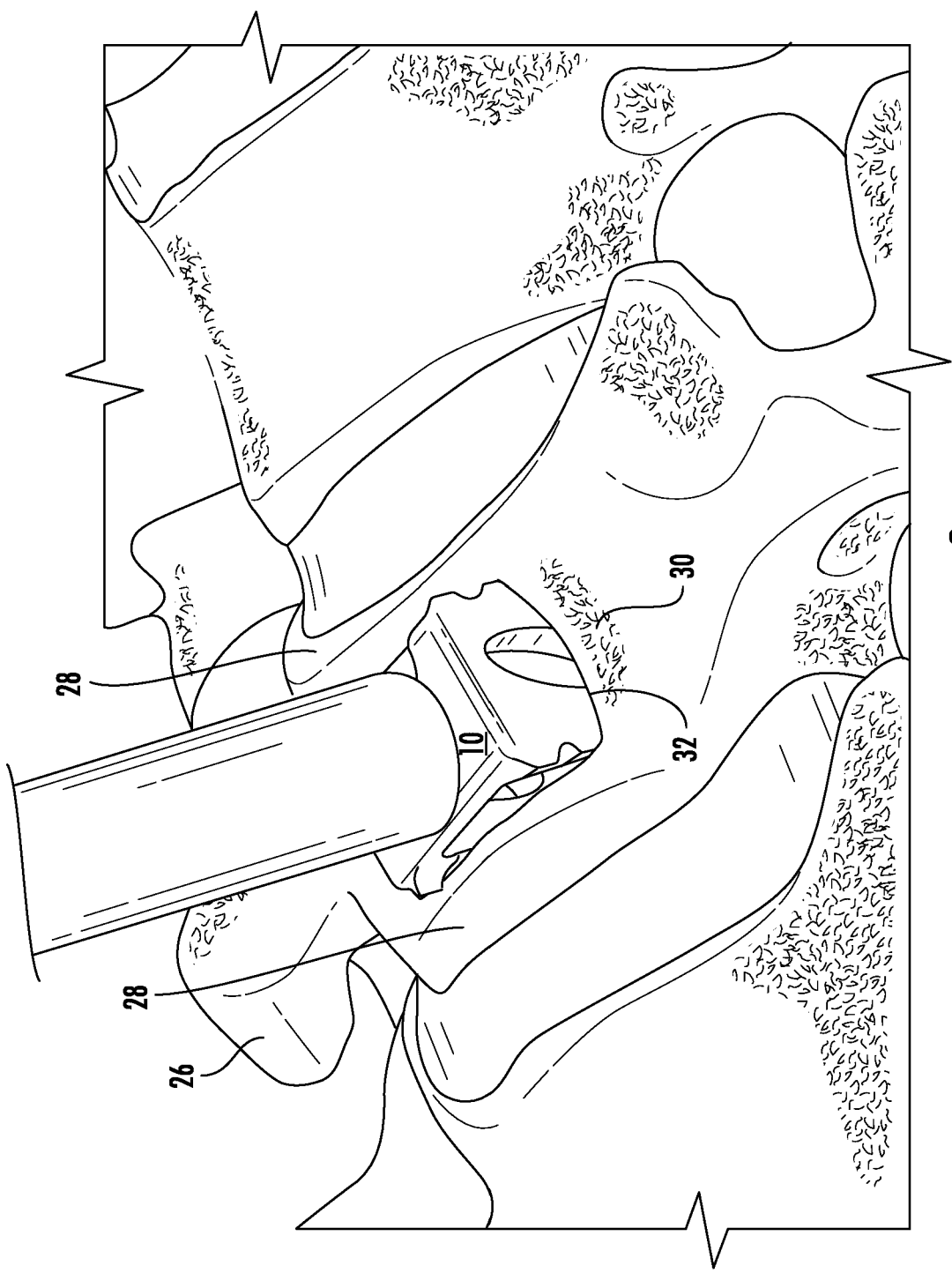
FIG. 8 illustrates the implant being inserted within the void in a single vertebra.

FIG. 8 shows implant 10 being inserted further within void 32. In FIG. 8, a greater portion of the mass of implant 10 is shown to be inserted into void 32 in vertebra 26. Thus, in another embodiment of the present disclosure, a greater portion of the mass of implant 10 resides within the confines of the transcorporeal defect, i.e., void 32, in vertebra 26. In other words, in this embodiment, greater than fifty percent of implant 10 is inserted within the confines of the vertebra 26.

Figure 9:
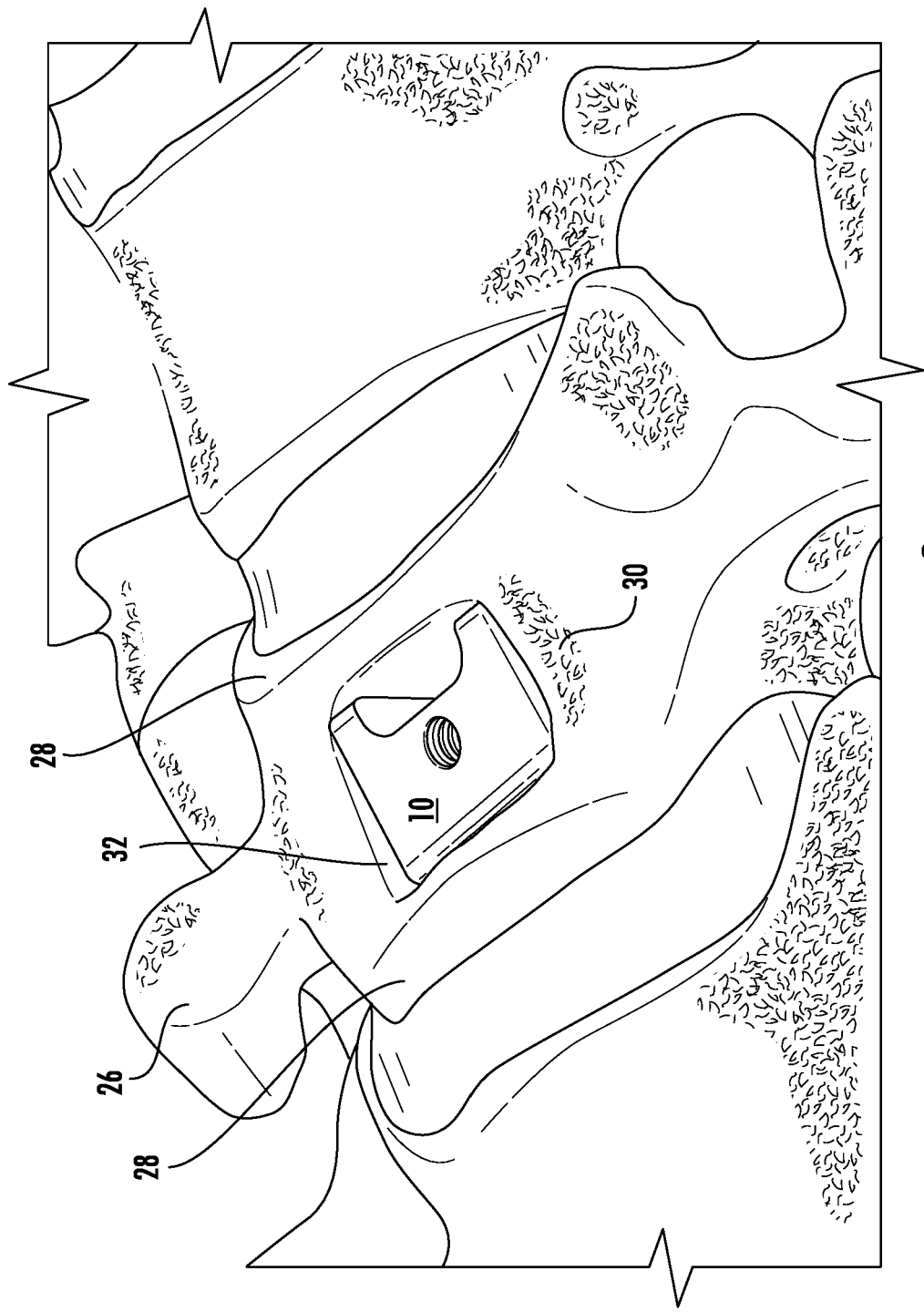
FIG. 9 illustrates the implant of the present disclosure fully inserted within the void in a single vertebra.

FIG. 9 shows the complete insertion of implant 10 within void 32. Advantageously, and unlike some prior implants, implant 10 of the present disclosure does not require any fixation or fixation apparatus mounted to the exterior of vertebra 26. Unlike other implants that require a feature that engages to the vertebra 26 into which implant 10 has been placed or that engages to adjacent vertebra such as bone plates and/or screws outside of the iatrogenically created vertebral defect, i.e., void 32, implant 10 of the present disclosure does not have such a requirement and can be inserted within void 32 as shown in FIG. 8 and FIG. 9 without the need of an external fixation device.

There are several reasons why there is no need for an external fixation apparatus or means to secure implant 10 within void 32. For example, because implant 10 includes open region 24 into which the patient's blood and cells are able to flow, implant 10 may be further secured within void 32 due to the integration of the patient's cells as described earlier. Thus, in this embodiment, the patient's own healing processes are used to further engage and secure implant 10.

Additionally, because implant 10, unlike most general spinal implants, is anteriorly placed between the superior and inferior endplates 28 of just one vertebra 26, there is no need for any external fixation mechanism, such as a bone plate or other external fixation mechanism.

Another reason why implant 10 does not require any external fixation, is because, in one embodiment, implant 10 is of a larger dimension than the dimension of the void 32 into which implant 10 is to be placed, as discussed above. Such a "friction fit" allows implant 10 to securely engage the interior surfaces of vertebra 26, even without the use of blades 22 or threads. In yet another embodiment, blades 22 or threads are used as an engagement mechanism to grasp or otherwise engage one or more of the interior surfaces of vertebra 26. Blades 22 can be designed of differing lengths and angles in order to accommodate different sized voids 32. When implant 10 is inserted within void 32, blades 22 "grasp" the inner surfaces of vertebra 26, thus preventing implant 10 from being inadvertently moved or jostled out of the confines of void 32. Thus, in comparison to general spinal implants placed anteriorly, implant 10 of the present disclosure is not structurally connected to any adjacent vertebra 26.

The confines of a vertebral body are defined as an area bounded by the outer remaining portions of the exterior aspect of a vertebral cortical bone wall of the vertebral body which is anterior to the spinal cord. This would also include the outer diameter of the vertebral endplate of a vertebra in the case wherein the exterior aspect of the vertebral cortical wall has been damaged or removed by trauma, disease, or surgical intervention. In other words, the confines of a vertebral body include the anatomy inside the borders of the most exterior portions of a vertebra anterior to the spinal cord.

In this view, the repair of any destabilization of the vertebra that may occur should be considered. Providing for the repair of any destabilization of the vertebra that may occur includes intraoperative destabilization, or destabilization that may occur later, after surgery but as a result of the iatrogenic disruption of the transcorporeal procedure. A larger transcorporeal pathway, and a transcorporeal pathway that does not place a requirement upon the surgeon to stay with a round or symmetrical hole, requires an implant capable of handling different loads, supporting areas that might be weakened if not supported, and properly occupying and supporting the areas of disrupted tissues and restoring a void of unpredicted shape. What is taught by the present disclosure is a transcorporeal approach that allows for a greater variation in intraoperative bone removal in the creation of the transcorporeal approach. This greater bone removal from vertebra 26 can now include, with implant 10, up to and including the removal of the entire vertebral body between the two endplates of a single vertebra.

In one embodiment, the size of implant 10, placed within the confines of vertebra 26, is equal to or greater than fifty percent of the shortest cross sectional measurement of vertebra 26 in at least two of the implant's dimensions. In other words, if vertebra 26 is measured as 16 mm across the width and that is the shortest cross sectional measurement of vertebra 26, implant 10 will be equal to or greater than 8 mm in at least two dimensions, i.e., the height and width of implant 10. The implant's "dimensions" may be, for example, its height, width, or length. Thus, in this scenario, implant 10 would have at least two of its three dimensions (the three dimensions being height, width, and length) equal to or greater than 8 mm in length. For example, the width of implant 10 could be 12 mm and the height of implant 10 could be 8 mm. Or, its width could be 8.5 mm and its length 11 mm.

In another example, if vertebra 26 measures 12 mm in height and that is the shortest cross sectional measurement of vertebra 26, implant 10 will be at least equal to or greater than 6 mm in at least two of the implant's dimensions. Finally, as another example, if the vertebra 26 measures 15 mm from the superior right corner to the inferior left corner, then, again, implant 10 will be equal to or greater than 7.5 mm in at least two of its dimensions.

In another embodiment, an implant 10 is provided for repairing a transcorporeal defect created in a vertebra during an anterior surgical procedure that provides greater than two axes of trajectory for bone removal and greater than two axes of trajectory for placement of implant 10. The ability of implant 10 to provide greater than two axes of trajectory is at least partially provided by the ability to insert implant 10 within void 32 without the need or use of an anterior bone plate. As implant 10 does not require a bone plate for trajectory guidance devices or fixation, implant 10 allows for wider, more diverse bone removal with a degree of freedom that is greater than the two axes methods permitted by implants that include a bone plate or other external fixation mechanisms. Therefore, what is disclosed herein, is an inventive implant 10 that, by being free of a required bone plate for fixation, allows for greater freedom for removal of bone in greater than two axes. In one embodiment, the disclosed implant 10 is for placement into a vertebral defect, where the defect is iatrogenically created during an anterior surgical transcorporeal procedure to the spine, the defect created between the two naturally occurring anatomical endplates of an individual vertebral body, the created defect beginning anteriorly and ending at a point beyond the posterior cortical wall of the vertebra, wherein placement of implant 10 into the transcorporeal defect is free of a requirement of an anterior plate separately attached to vertebra 26. The feature of the implant 10 being unencumbered by a fixed guidance mechanism provides for the additional feature of greater than two axes of directional freedom upon placement of the implant 10 into the void created during the performance of the transcorporeal procedure.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of placing an implant into an iatrogenically created spinal defect to the spine, the method comprising:
   creating a void in a vertebral body of a vertebra, the void beginning anteriorly and directed posteriorly creating an exit at a back of the vertebral body; and
   placing the implant into the void between a superior endplate and an inferior endplate of the vertebra, the implant being non-cylindrical.

2. A method of placing an implant into an iatrogenically created spinal defect to the spine, the method comprising:
   creating a void in the vertebral body directed toward a greater epidural space thereby creating an exit at a back of the vertebral body;
   working through the void during a surgery, utilizing an anterior approach;
   placing the implant into the void between a superior endplate and an inferior endplate of the vertebra, the implant being non-cylindrical.

3. The method of claim 2, further comprising working through a vertebral body of a vertebra during a surgery utilizing an anterior approach without fusing two vertebrae together.

* * * * *